US010729741B2

(12) United States Patent
Clark et al.

(10) Patent No.: US 10,729,741 B2
(45) Date of Patent: Aug. 4, 2020

(54) METHODS OF TREATING BURNS WITH I.V. CP12 IN A WINDOW FROM 2 TO 6 HOURS AFTER INJURY

(71) Applicant: NeoMatrix Therapeutics Inc., Stony Brook, NY (US)

(72) Inventors: Richard August Clark, Setauket, NY (US); Fubao Lin, Stony Brook, NY (US)

(73) Assignee: NeoMatrix Therapeutics Inc., Stony Brook, NY (US)

( * ) Notice: Subject to any disclaimer, the term of this patent is extended or adjusted under 35 U.S.C. 154(b) by 0 days.

(21) Appl. No.: 15/469,988

(22) Filed: Mar. 27, 2017

(65) Prior Publication Data

US 2018/0271934 A1      Sep. 27, 2018

(51) Int. Cl.
*A61K 38/12* (2006.01)
*A61K 38/39* (2006.01)
*A61K 9/00* (2006.01)

(52) U.S. Cl.
CPC ............ *A61K 38/12* (2013.01); *A61K 9/0019* (2013.01); *A61K 38/39* (2013.01)

(58) Field of Classification Search
None
See application file for complete search history.

(56) References Cited

U.S. PATENT DOCUMENTS

| 4,179,337 | A | 12/1979 | Davis et al. |
| 4,301,144 | A | 11/1981 | Iwashita et al. |
| 4,496,689 | A | 1/1985 | Mitra |
| 4,522,811 | A | 6/1985 | Eppstein et al. |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,939,239 | A | 7/1990 | Matsuhashi et al. |
| 5,051,448 | A | 9/1991 | Shashoua |
| 5,053,388 | A | 10/1991 | Gibson et al. |
| 5,166,320 | A | 11/1992 | Wu et al. |
| 5,169,862 | A | 12/1992 | Burke, Jr. et al. |
| 5,192,746 | A | 3/1993 | Lobl et al. |
| 5,270,168 | A | 12/1993 | Grinnell |
| 5,283,173 | A | 2/1994 | Fields et al. |
| 5,288,514 | A | 2/1994 | Ellman |
| 5,359,115 | A | 10/1994 | Campbell et al. |
| 5,362,899 | A | 11/1994 | Campbell |
| 5,539,085 | A | 7/1996 | Bischoff et al. |
| 5,559,103 | A | 9/1996 | Gaeta et al. |
| 5,576,423 | A | 11/1996 | Aversa et al. |
| 6,799,657 | B2 | 10/2004 | Daniels |
| 6,808,923 | B2 | 10/2004 | Engelman et al. |
| 6,818,209 | B1 | 11/2004 | Mitrophanous et al. |
| 6,830,892 | B2 | 12/2004 | Marasco et al. |
| 6,863,884 | B2 | 3/2005 | Schauber et al. |
| 6,924,123 | B2 | 8/2005 | Kingsman et al. |
| 7,105,341 | B2 | 9/2006 | Kinsella |
| 8,691,944 | B2 * | 4/2014 | Clark ................... A61K 8/02 530/326 |
| 8,759,300 | B2 * | 6/2014 | Clark ................... A61L 27/227 424/78.06 |
| 2004/0120918 | A1 | 6/2004 | Lintner et al. |
| 2005/0025725 | A1 | 2/2005 | Clark et al. |
| 2005/0282747 | A1 | 12/2005 | Schultz et al. |
| 2006/0038778 | A1 | 2/2006 | Boon et al. |
| 2010/0292161 | A1 | 11/2010 | Clark |

FOREIGN PATENT DOCUMENTS

| WO | 9107087 | 5/1991 |
| WO | 9210092 | 6/1992 |
| WO | 9309668 | 5/1993 |
| WO | 9320242 | 10/1993 |
| WO | 9408951 | 4/1994 |
| WO | 02090377 | 11/2002 |
| WO | 03016337 | 2/2003 |
| WO | 2005009510 | 2/2005 |
| WO | 2005117936 | 12/2005 |
| WO | 2007044396 | 4/2007 |

OTHER PUBLICATIONS

Le Tourneau, Christophe et al, "Dose escalation methods in phase I cancer clinical trials." J. Natl. Canc. Inst. (2009) 101 p. 708-720.*
Oda, Jun et al, "Effect of intravenous atrial natriuretic peptide on pulmonary dysfunction and renal function following burn shock." J. Trama (2009) 66 p. 1281-1285.*
Pan, Shin-Chen, "Burn blister fluids in the neovascularization stage of burn wound healing: a comparison between superficial and deep partial thickness burn wounds." Burns Trauma (2013) 1(1) p. 27-31.*
La Celle, Peter et al, "Blood-borne collagenous debris complexes with plasma fibronectin after thermal injury," Blood (1990) 75(2) p. 470-478.*
Kleiber, Max; "Body size and metabolic rate." Physiol. Rev. (1947) 27(4) p. 511-541.*
Ambesi et al. "Anastellin, a Fragment of the First Type III Repeat of Fibronectin, Inhibits Extracellular Signal-Regulated Kinase and Causes G1 Arrest in Human Microvessel Endothelial Cells" Cancer Research, 65(1):148-156 (2005).
Asif et al. "Blood vessel occlusion in peri-burn tissue is secondary to erythrocyte aggregation and mitigated by a fibronectin-derived peptide that limits burn injury progression" Wound Repair and Regeneration, 24:501-513 (2016).
Clark et al. "Blood Vessel Fibronectin Increases in Conjunction with Endothelial Cell Proliferation and Capillary Ingrowth During Wound Healing" The Journal of Investigative Dermatology, 79(5):269-276 (1982).
Clark et al. "Fibronectin and Fibrin Provide a Provisional Matrix for Epidermal Cell Migration During Wound Reepithelialization" The Journal of Investigative Dermatology, 79(5):264-269 (1982).

(Continued)

Primary Examiner — Fred H Reynolds
(74) Attorney, Agent, or Firm — Myers Bigel, P.A.

(57) ABSTRACT

A treatment window for the intravenous treatment of wounds, including thermal and chemical burns, with cP12 is presented. In particular, Applicants have unexpectedly found that delaying intravenous treatment with fibronectin-derived peptides, such as cP12, from 2 to 6 hours, particularly about 4 hours, after wounding, provides superior wound-closing results than treatment at 1 hour or after 8 or more hours.

8 Claims, No Drawings
Specification includes a Sequence Listing.

(56) References Cited

OTHER PUBLICATIONS

Clark et al. "Fibronectin is produced by blood vessels in response to injury" The Journal of Experimental Medicine, 156(2):646-651 (1982).

Clark et al "Fibronectin Beneath Reepithelializing Epidermis in Vivo: Sources and Significance" The Journal of Investigative Dermatology, 80(6 suppl.):26S-30S (1983).

Clark et al. "Either exogenous or endogenous fibronectin can promote adherence of human endothelial cells" Journal of Cell Science, 82:263-280 (1986).

Clark et al. "Collagen matrices attenuate the collagen synthetic response of cultured fibroblasts to TGF-β" Journal of Cell Science, 108:1251-1261 (1995).

Clark et al. "Fibroblast Migration on Fibronectin Requires Three Distinct Functional Domains" The Journal of Investigative Dermatology, 121(4):695-705 (2003).

Clark et al. "Tissue Engineering for Cutaneous Wounds" The Journal of Investigative Dermatology, 127 (5):1018-1029 (2007).

Danilenko et al. "Growth Factors in Porcine Full and Partial Thickness Burn Repair" American Journal of Pathology, 147(5):1261-1277 (1995).

Frame et al. "Vasoactive effect of fibronectin-derived epiviosamine-1 and related peptides in quiescent and stress models" Microcirculation, 24:e12369 (2017).

Gailit et al. "Studies in Vitro on the Role of alpha v and beta 1 Integrins in the Adhesion of Human Dermal Fibroblasts to Provisional Matrix Proteins Fibronectin, Vitronectin, and Fibrinogen" The Journal of Investigative Dermatology, 106 (1):102-108 (1996).

Garcia et al. "Modulation of Cell Proliferation and Differentiation through Substrate-dependent Changes in Fibronectin Conformation" Molecular Biology of the Cell, 10(3):785-798 (1999).

Greenhalgh et al. "PDGF and FGF Stimulate Wound Healing in the Genetically Diabetic Mouse" American Journal of Pathology, 136(6):1235-1246 (1990).

Greiling et al. "Fibronectin provides a conduit for fibroblast transmigration from collagenous stroma into fibrin clot provisional matrix" Journal of Cell Science, 110(Pt. 7):861-870 (1997).

Grinnell et al. "Degradation of Fibronectin and Vitronectin in Chronic Wound Fluid: Analysis by Cell Blotting, Immunoblotting and Cell Adhesion Assays" The Journal of Investigative Dermatology, 98:410-416 (1992).

Gui et al. "Identification of the Heparin-binding Determinants within Fibronectin Repeat IIII" The Journal of Biological Chemistry, 281(46):34816-34825 (2006).

International Search Report corresponding to International Patent Application No. PCT/US2006/038778 (2 pages) (dated Jul. 11, 2008).

International Search Report corresponding to International Patent Application No. PCT/US2017/056399 (4 pages) (dated Jan. 24, 2018).

Kouki et al. "Highly constrained cyclic (S,S)—CXaaC– peptides as inhibitors of fibrinogen binding to platelets" Journal of Thrombosis and Haemostasis, 3(10):2323-2330 (2005).

Lin et al. "Fibronectin Peptides that Bind PDGF-BB Enhance Survival of Cells and Tissue under Stress" The Journal of Investigative Dermatology, 134(4):1119-1127 (2014).

Maile et al. "The Heparin Binding Domain of Vitronectin Is the Region that Is Required to Enhance Insulin-Like Growth Factor-I Signaling" Molecular Endocrinology, 20(4):881-892 (2006).

Miyamoto et al. "Integrins Can Collaborate with Growth Factors for Phosphorylation of Receptor Tyrosine Kinases and MAP Kinase Activation: Roles of Integrin Aggregation and Occupancy of Receptors" The Journal of Cell Biology, 135(6):1633-1652 (1996).

Sottile et al. "Fibronectin Polymerization Regulates the Composition and Stability of Extracellular Matrix Fibrils and Cell-Matrix Adhesions" Molecular Biology of the Cell, 13:3546-3559 (2002).

Wijelath et al. "Novel Vascular Endothelial Growth Factor Binding Domains of Fibronectin Enhance Vascular Endothelial Growth Factor Biological Activity" Circulation Research, 91(1):25-31 (2002).

Wijelath et al. "Heparin-II Domain of Fibronectin Is a Vascular Endothelial Growth Factor-Binding Domain" Circulation Research, 99(8):850-860 (2006).

Xu et al. "Extracellular Matrix Alters PDGF Regulation of Fibroblast Integrins" The Journal of Cell Biology, 132:239-249 (1996).

Hirth et al. "Endothelial necrosis at 1h post-burn predicts progression of tissue injury" Wound Repair & Regeneration, 21(4):563-570 (2013).

Lin et al. "Fibronectin Growth Factor-Binding Domains Are Required for Fibroblast Survival" Journal of Investigative Dermatology, 131:84-98 (2011).

Lanier et al. "Spatiotemporal progression of cell death in the zone of ischemia surrounding burns" Wound Repair and Regeneration, 19:622-632 (2011).

Singer et al. "Validation of a Vertical Progression Porcine Burn Model" Journal of Burn Care and Research, 32 (6):638-646 (2011).

* cited by examiner

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: a 14-residue peptide that is cryptic within the
      immunoglobulin sandwich type of beta-pleated sheet of
      fibronectin's first type
      III repeat

<400> SEQUENCE: 1

Pro Ser His Ile Ser Lys Tyr Ile Leu Arg Trp Arg Pro Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: a cyclized form of a 14-residue peptide that is
      cryptic within the immunoglobulin sandwich type of beta-pleated
      sheet of fibronectin's first type III repeat

<400> SEQUENCE: 2

Pro Ser His Ile Ser Lys Tyr Ile Leu Arg Trp Arg Pro Lys
1               5                   10
```

METHODS OF TREATING BURNS WITH I.V. CP12 IN A WINDOW FROM 2 TO 6 HOURS AFTER INJURY

GOVERNMENT SUPPORT

This invention was made with government support under contract number W81XWH-08-2-0034 awarded by U.S. Army Medical Research and Material Command (USAM-RMC). The government has certain rights in the invention.

TECHNICAL FIELD

This invention is based on the discovery of that treatment of wounds, including burns, by i.v. treatment with known polypeptides derived from fibronectin, such as cP12 (SEQ ID NO:2), is improved by delaying treatment for at least two hours from the time of wounding.

BACKGROUND

In the US civilian population, each year, approximately 500,000 patients with burns present to emergency departments. Of 40,000 annual hospital admissions, 25,000 burn victims are admitted to specialized burn centers. Average time between burn injury and arrival at a hospital, in the United States, is approximately four hours. Progressive extension of burns can have a devastating effect. Over the course of a few days to one week deep partial-thickness burns can become full-thickness burns, which in the short term, leads to increased tissue loss, longer healing time, excess morbidity and mortality. In the long term, increased scarring, wound contractures and poor quality of life become major issues. While the exact mechanism(s) leading to conversion of the zone of ischemia to full-blown necrosis is unclear, several processes, including oxidant and cytokine stress resulting from inflammation as well as ischemia/reperfusion, probably play a role. Therapies to improve blood flow, such as non-steroidal anti-inflammatory agents (NSAIDS) and anti-coagulants (heparin) have not shown substantial benefit in preventing burn injury progression. Hence therapy to limit burn injury progression is an unmet need.

There is evidence that fibronectin (FN) is involved in many biological processes including tissue repair, embryogenesis, cell migration, wound repair, and cell adhesion. There are two primary forms of fibronectin. The first is an insoluble glycoprotein dimer that serves as a linker in the extracellular matrix (ECM), and the second is a soluble disulfide-linked dimer found in plasma. The ECM form of fibronectin is expressed by fibroblasts, chondrocytes, endothelial cells, macrophages and certain epithelial cells. The plasma form of fibronectin is expressed by hepatocytes. Fibronectin can serve as a general cell adhesion molecule by anchoring cells to collagen or to proteoglycan substrates. Fibronectin can also play a role in organizing cellular interactions by binding to components of the ECM and to membrane-bound fibronectin receptors on cell surfaces. Forms of fibronectin are found in vertebrates, including mammals, birds, amphibians, fish, and reptiles.

FN, a 500 kDa glycoprotein, circulates in the blood and is produced and deposited by tissue cells in the provisional extracellular matrix (ECM) during tissue formation. As a critical component of the provisional ECM, FN plays a vital role in embryogenesis, morphogenesis and wound healing but is deficient in burn patients' wounds and blood. FN is known to be degraded in burn wound fluids by the endopeptidase neutrophil elastase. See Grinnell, et al, Identification of Neutrophil Elastase as the Proteinase in Burn Wound Fluid Responsible for Degradation of Fibronectin, *J Invest. Dermatology*, 1994, 103(2):155-61.

Previously disclosed peptide "P12" is 14-residue peptide that is cryptic within the immunoglobulin sandwich type of β-pleated sheet of fibronectin's (FN) first type III repeat (FNIII$_1$). Unlike FN, P12 in solution promotes mesenchymal cell growth, proliferation and migration intrinsically and synergistically with a variety of growth factors, especially platelet-derived growth factor-BB (PDGF-BB). Furthermore, P12 protects adult human dermal fibroblasts (AHDF) from cell death induced by oxidative and cytokine stress and/or nutrient withdrawal in the presence of PDGF-BB. P12 also limits burn injury progression in rat and porcine burn models and mitigates scarring in a vertical burn injury progression pig model. See, e.g., PCT/US2006/038778; U.S. Pat. No. 8,759,300; Lin, et al, Fibronectin peptides that bind PDGF-BB enhance survival of cells and tissue under stress, *J Invest Dermatol*. 2014 April; 134(4): 1119-1127; and Asif, et al., Blood Vessel Occlusion in Peri-burn Tissue is Secondary to Erythrocyte Aggregation and Mitigated by a Fibronectin-derived Peptide that Limits Burn Injury Progression, *Wound Rep Reg* (2016) 24 501-513. In particular, the fragment of fibronectin PSHISKYILRWRPK SEQ ID NO:1, or "P12", and a cyclized version of the polypeptide PSHISKYILRWRPK SEQ ID NO:2, or "cP12", is disclosed U.S. Pat. No. 8,759,300, Lin, et al., and Asif, et al. as being useful for the treatment of wounds, particularly the treatment of burns. U.S. Pat. No. 8,759,300 is hereby incorporated, herein, in its entirety.

Citation of a reference in this section is not to be interpreted as an admission that the reference is prior art under 35 U.S.C. § 102 and/or 103.

SUMMARY

We present the intravenous ("i.v.") treatment of wounds with peptides derived from fragments of fibronectin, particularly cP12 (SEQ ID NO: 2), in a window from at about 2 hours after wounding to about 6 hours after wounding. In particular, we have discovered that wound, including burn, treatment with peptides derived from fibronectin fragments is unexpectedly improved if delayed between 2 and 6 hours. In one embodiment, a chemical or thermal burn is treated by the intra venous administration of between 0.003 and 0.1 mg/kg cP12 (SEQ ID NO: 2) about 4 hours after the burn occurs. In one embodiment, the intravenous treatment has about a half hour duration. In one embodiment, a chemical or thermal burn is treated by the intravenous administration of between 0.03 and 0.01 mg/kg cP12 (SEQ ID NO: 2) in a treatment window from about 2 hours after wounding to about 6 hours after wounding.

We have discovered that previously disclosed, biologically active, peptide fragments of fibronectin, such as cyclized P12 (SEQ ID NO:2), when used as an i.v. treatment, are more effective when administered 2 to 6 hours after wounding, than when administered at one hour or from 8 to 12 hours after wounding. This delayed, best treatment window is surprising and clinically useful, since getting burn patients to a facility, such as a hospital, capable of advanced treatments, such as i.v. polypeptide administration, less than 2 hours after injury is logistically difficult. Applicants have no biological explanation for why the treatment delayed for 2-6 hours, particularly 4 hours, is more effective than treatment one hour after the wounding.

The wounds to be treated include surgical incision or extirpation, a traumatic injury, a thermal burn, a chemical burn, a lesion or ulceration of the patient's skin, mucosa, connective tissue, fascia, ligament, tendon, cartilage, nerve or muscle and a wound to the patient's bone. The treated wounds may be infected or uninfected. In a particular embodiment, the wounds to be treated are thermal and/or chemical burns.

DETAILED DESCRIPTION

The details of one or more embodiments of the invention are set forth in the accompanying drawings and the description below. Other features, objects, and advantages of the invention will be apparent from the description and drawings, and from the claims.

All peptides described herein are presented in a linear format of standard, single-letter amino acid codes, reading from the N terminus on the left to the C terminus on the right. "Cyclic" or "cyclized" peptides may be represented in linear form but have the N terminus amino acid bound to the C terminus amino acid by one or more standard methods, described below. The form of cyclized P12 used in the experiments below was made by formation of a peptide bond between the carboxy and amino-terminal ends of the linear peptide PSHISKYILRWRPK SEQ ID NO:2.

The fragments can be contained within physiologically acceptable compositions, or they may be contained within compositions that are not suitable for administration to a living being (e.g., concentrated stocks or frozen or lyophilized compositions).

The methods of the invention include methods for promoting wound healing. These methods include a step of administering to a patient a therapeutically effective amount of a pharmaceutical composition comprising a fragment of fibronectin, or a biologically active variant thereof, as described herein. The fragment of fibronectin, or the biologically active variant thereof, can be present in a complex with one or more growth factors. The methods can optionally include a step of identifying a patient in need of treatment. Such patients include patients who are suffering from a surgical extirpation or incision of the skin, mucosa, underlying connective tissue, fascia, ligament, tendon, cartilage, bone, nerve or muscle; patients who are suffering from a traumatic laceration or tissue loss of the skin, mucosa, underlying connective tissue, fascia, nerve or muscle; and patients who are suffering from a thermal burn, chemical burn, or ulceration of the skin, mucosa, underlying connective tissue, fascia, nerve or muscle.

As used herein, a "burn" is tissue damage due to exposure to heat or a caustic chemical. A "thermal burn" is tissue damage due to exposure to heat. A "chemical burn" is tissue damage due to exposure to a caustic chemical, often strong alkali or strong acid. Agents of chemical burns to be treated by the peptides defined by the invention include, but are not limited to, phenol, creosol, mustard gas, phosphorus, nitrogen mustard, arsenic compounds, ammonia, caustic potash, lime, sodium hydroxide, hydrochloric acid, and sulphuric acid.

Suitable formulations are described further below and, generally, take the form of a solution.

As detailed above, we have found, inter alia, that specific fragments of fibronectin and peptides derived from fibronectin can bind various growth factors (e.g., IGF-1, HGF, TGF-β1, TGF-β2, bFGF, FGF-7, PDGF-BB, VEGF-A, or NGF), and the bound growth factors can retain a biological activity. The present invention features compositions that include such fragments and peptides, with or without bound growth factors in the represented families (i.e., in the IGF, TGF, FGF, PDGF, VEGF, and NGF families), in various formulations and configurations. The fragments and peptides may promote synergy with GFs to which the FN fragments or peptides do not bind. In one configuration, the FN fragments or peptides, or FN fragment or peptide/GF-containing complexes can be incorporated into engineered two- or three-dimensional extracellular matrices (which we may abbreviate herein as engECM or refer to as synthetic matrices), and these can include any of; or any combination of, the peptides described herein (e.g., a peptide conforming to Formulas I) or biologically active variants thereof. The growth factor(s) incorporated can be, for example, IGF-1, TGF-β1, TGF-β2, bFGF, FGF-7, PDGF-BB, VEGF-A, or NGF; any combination or sub-combination thereof; or another specific growth factor in the same family as those listed. The growth factors can be exogenously added to the peptide-containing formulation (e.g., a FN fragment-containing matrix), or the formulation (e.g., the matrix) can be generated without growth factors.

For preparation of pharmaceutical compositions containing one or more of the present peptides, for therapeutic treatments, the active ingredients (e.g., the peptide alone or the peptide bound to GF(s)) can be incorporated alone or in combination with other active agents into compositions suitable for administration to a patient. The formulations can be made using methods routine in the art and particular guidance may be provided by prior formulations of protein-based therapeutics. The compositions will be physiologically acceptable (i.e., substantially non-toxic) and may be formulated as prescription medications or over-the-counter products. Pharmaceuticals or pharmaceutically acceptable compositions contain compounds (e.g., polypeptides), other materials (e.g., diluents), and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Modifications of Peptides:

The featured fragments and biologically active variants thereof can be modified in numerous ways. For example, agents, including additional amino acid residues, other substituents, and protecting groups can be added to either the amino terminus, the carboxy terminus, or both. The modification can be made for the purpose of altering the fragments' form or altering the way the fragments bind to or interact with one another, with non-identical fragments, or with other polypeptides. While the peptides of the present invention may be linear or cyclic, cyclic peptides generally have an advantage over linear peptides in that their cyclic structure is more rigid and hence their biological activity may be higher than that of the corresponding linear peptide (see, generally, Camarero and Muir, J. Am. Chem. Soc. 121:5597-5598, 1999).

Strategies for the preparation of circular polypeptides from linear precursors have been described and can be employed with the present fragments. For example, a chemical cross-linking approach can be used to prepare a backbone cyclized version of the peptide (Goldenburg and Creighton, J. Mol. Biol., 165:407-413, 1983). Other approaches include chemical intramolecular ligation methods (see, e.g., Camarero et al., Angew. Chem. Int. Ed., 37:347-349, 1998; Tam and Lu, Prot. Sci., 7:1583-1592, 1998; Camarero and Muir, Chem. Commun., 1997:1369-1370, 1997; and Zhang and Tam, J. Am. Chem. Soc.

119:2363-2370, 1997) and enzymatic intramolecular ligation methods (Jackson et al., J. Am. Chem. Soc., 117:819-820, 1995), which allow linear synthetic peptides to be efficiently cyclized under aqueous conditions. See also U.S. Pat. No. 7,105,341.

Alternatively, or in addition, any of the present fragments can further include one or more substituents. For example, the fragment can include a substitutent at the amino-terminus, carboxy-terminus, and/or on a reactive amino acid residue side-chain. The substituent can be an acyl group or a substituted or unsubstituted amine group (e.g., the substituent at the N-terminus can be an acyl group and the C-terminus can be amidated with a substituted or unsubstituted amine group (e.g., an amino group having one, two, or three substituents, which may be the same or different)). The amine group can be a lower alkyl (e.g., an alkyl having 1-4 carbons), alkenyl, alkynyl, or haloalkyl group. The acyl group can be a lower acyl group (e.g., an acyl group having up to four carbon atoms), especially an acetyl group. The substituent can be a non-protein polymer, for example, a polyether, a polyethylene glycol (PEG), a polypropylene glycol, or a polyoxyalkylene, a polyalkylene glycol (for example, polypropylene glycol (PPG), a polybutylene glycol (PBG), or a PPG-PEG block/random polymer. The peptide can be modified by a non-protein polymer by methods known in the art and in the manner set forth in U.S. Pat. Nos. 4,640,835; 4,496,689; 4,301,144; 4,670,417; 4,791,192 or 4,179,337. The modification (e.g., PEGylation) can stabilize the peptide, reduce its antigenicity, decrease the required dosage, and/or augment its targeting ability.

The non-protein polymer can vary in size and shape. For example, any of the non-protein polymers listed above (e.g., PEG) can be linear, branched, or comb-shaped. Regarding size, the molecular weight can vary. For example, the PEG can have a molecular weight of, for example, about 300 kDa, about 1,000 kDa, about 2,000 kDa, about 3,000 kDa, about 4,000 kDa, about 5,000 kDa, about 6,000 kDa, about 7,000 kDa, about 8,000 kDa, about 9,000 kDa, about 10,000 kDa, about 11,000 kDa, about 12,000 kDa about 13,000 kDa about 14,000 kDa about 15,000 kDa, about 20,000 kDa, about 30,000 kDa, about 40,000 kDa, or about 50,000 kDa. For example, the PEG can be of a molecular weight anywhere in between 300 kDA and 2000 kDA, 300 kDA and 3000 kDA, 1000 kDA and 2000 kDA and 1000 and 3000 kDA.

The non-protein polymer (e.g., PEG) can be linked to the fragment by any number of functional group chemistries (e.g., carboxylated-mPEGs, p-nitrophenyl-PEGs, aldehyde-PEGs, amino-PEGs, thiol-PEGs, maleimide-PEGs, aminoxy-PEGs, hydrazine-PEGs, tosyl-PEGs, iodoacetamide-PEGs, succinimidylsuccinate-PEGs, succinimidylglutarate-PEGS, succinimidylcarboxypentyl-PEGs, p-nitrophenycarbonate-PEGs, or ethanethiol-PEGs). The non-protein polymer (e.g., PEG) can be linked to the fragment through any number of chemical groups including, but not limited to, amino-terminal amino acids, carboxy-terminal amino acids, free amines, and free sulfhydryl groups.

The non-protein polymer (e.g., PEG) may be a functionalized (for example, a monofunctional activated linear PEG, a homobifunctional activated linear PEG, a heterobifunctional activated linear PEG, a multiarmed activated PEG (e.g. 2-armed, 4-armed, 8-armed, etc.), a branched activated PEG and a comb-shaped activated PEG).

As used herein, the term "alkyl" is meant to refer to a saturated hydrocarbon group, which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like. "Alkynyl" refers to an alkyl group having one or more triple carbon-carbon bonds. Example alkynyl groups include ethynyl, propynyl, and the like. "Haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "polyether" refers to a polymer containing ether linkages. Examples include polyethylene glycol.

The fragments, including the modified fragments described above, can be protease resistant and can include one or more types of protecting groups such as an acyl group, an amide group, a benzyl or benzoyl group, or a polyethylene glycol. More specifically, a fragment, including the modified fragments described above, can be N-terminally acetylated and/or C-terminally amidated.

Where non-naturally occurring or modified amino acid residues are included they can be selected from the following or many others available in the art: 4-hydroxyproline, gamma-carboxyglutamic acid, o-phosphoserine, o-phosphotyrosine, or delta-hydroxylysine. Other examples include naphthylalanine, which can be substituted for tryptophan to facilitate synthesis, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. Fragments having non-naturally occurring amino acid residues may be referred to as synthetic fragments and constitute one type of variant as described herein. Other variants include fragments in which a naturally occurring side chain of an amino acid residue (in either the L- or D-form) is replaced with a non-naturally occurring side chain.

For guidance on fragment modification by reduction/ alkylation and/or acylation, one can consult Tarr, Methods of Protein Microcharacterization, J. E. Silver ed., Humana Press, Clifton N.J. 155-194, 1986; for guidance on chemical coupling to an appropriate carrier, one can consult Mishell and Shiigi, eds, Selected Methods in Cellular Immunology, WH Freeman, San Francisco, Calif. (1980) and U.S. Pat. No. 4,939,239; and for guidance on mild formalin treatment, one can consult Marsh, Int. Arch. of Allergy and Appl. Immunol., 41:199-215, 1971.

Physiologically Acceptable Compositions:

A present pharmaceutical composition is formulated to be compatible with its intended route of administration, for example, intravenous.

Pharmaceutical compositions adapted for infusion include, for example, sterile aqueous solutions (where water soluble) or dispersions and sterile powders for the extemporaneous preparation of sterile infusible solutions. For intravenous administration, suitable carriers include, for example, physiological saline, bacteriostatic water, Cremophor EL™ (BASF, Parsippany, N.J.), albumin-containing solutions and phosphate buffered saline (PBS). In all cases, the compositions prepared for administration should be sterile and should be fluid or convertible to a fluid at least sufficient for easy use in an intrevenous infusion bag. The composition should be stable under the conditions of manufacture and storage and should be preserved against the contaminating action of microorganisms such as bacteria and fungi. Preservatives against microorganisms can include various antibacterial and antifungal agents, for example, parabens, chlorobutanol, phenol, ascorbic acid, thimerosal, and the like.

The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersions and by the use of surfactants.

In many cases, it will be desirable for the composition to be isotonic to blood. This can be accomplished using various isotonic agents, for example, sugars, polyalcohols such as manitol, sorbitol, sodium chloride in the composition.

It is especially advantageous to formulate parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. In one embodiment, the dosage unit form is about 0.1 to 5 mg of lyophilized peptide or peptide derivative. In another embodiment, the dosage unit form is about 1 mg of lyophilized peptide or peptide derivative.

Toxicity and therapeutic efficacy of active compounds and pharmaceutical compositions can be determined by standard pharmaceutical procedures in cell cultures or experimental animals. For example, such procedures are routinely applied for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are generally preferred. The data obtained from the cell culture assays and animal studies (including those described in the examples, below) can be used in formulating a range of dosage for use in humans or other intended subjects. The dosage of such compounds is usually selected to produce a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. Thus, for example, a dose may be initially established in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography, or by other suitable analysis method adapted for the compound of interest.

Depending on the animal type, cP12 (SEQ ID NO:2) (or linear P12. SEQ ID NO:1) can induce an anaphylactoid response at 2.5 to 10 mg/kg given as an iv bolus or even a rapid infusion. This reaction is less likely with a slower infusion. We have successfully used a 30 min infusion in pig models to avoid any anaphylacoid response.

Methods of Use:

The invention features methods for promoting tissue regeneration with a peptide derivative of a fibronectin fragment, such as cP12 (SEQ ID NO:2), including, for example, wound healing. As used herein, tissue regeneration is used to refer to the replacement of damaged tissue by the proliferation and differentiation of cells into a tissue. Tissue damage can occur by any means, including physical injury, disease, and infection. As described herein, "wound-healing" is used as a non-limiting example of tissue regeneration.

The primary goal in the treatment of wounds is to achieve wound closure. Open cutaneous wounds represent one major category of wounds and include thermal and/or chemical burn wounds, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age (see Hunt and Goodson in Current Surgical Diagnosis & Treatment (Way; Appleton & Lange), pp. 86-98, 1988). A "closed wound" is defined as a wound with 100% epithelialization.

The term "wound" refers broadly to injuries to the skin and subcutaneous tissue initiated in different ways (e.g., pressure sores from extended bed rest and wounds induced by trauma) and with varying characteristics as well as to injuries of other tissues and bone, including tissues and bone in or around the vicinity of a primary wound site. Of course, wounds can also be made surgically or by disease (e.g. cancer). Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include thermal or chemical burn wounds, pressure sores, venous stasis ulcers, and diabetic ulcers. The term "deep wound" is meant to include both Grade III and Grade IV wounds. The present invention contemplates treating all wound types, including deep wounds and chronic wounds.

The phrases "promote wound healing," "enhance wound healing," and the like refer to either the induction of the formation of granulation tissue of wound contraction and/or the induction of epithelialization (i.e., the generation of new cells in the epithelium). Wound healing is conveniently measured by decreasing wound area. It is not intended that phrases such as "promote wound healing" or "enhance wound healing" require a quantitative comparison with controls. In the case of treatment of a chronic wound, it is sufficient that evidence of wound healing begin after treatment. Many traumatic wounds and cancer extirpations must be left open to heal by secondary intention, and patients having such wounds and extirpations can be treated with the compositions described herein that promote wound healing.

The phrase "therapeutically effective amount" of the fibronectin fragments or peptide derivatives of fibronectin fragments of the invention, when referring to wound healing, promoting wound healing or enhancing wound healing, is that amount that promotes induction of the formation of granulation tissue of wound contraction and/or the induction of epithelialization. For example, fibronectin fragments or peptide derivatives of fibronectin fragments of the invention can be used to promote would healing in i.v. formulations in a amount of from about 0.1 µg/kg to about 1 mg/kg of patient body weight; in some embodiments, from about 1 µg/kg to about 1 mg/kg of patient body weight; in some embodiments, from about 1 µg/kg to about 0.1 mg/kg of patient body weight; in some embodiments, from about 0.01 mg/kg to about 1 mg/kg of patient body weight; and in some embodiments, from about 0.01 mg/kg to about 0.1 mg/kg of patient body weight.

In one method of use, a patient with a wound is treated intravenously with between 0.003 and 0.1 mg/kg of cP12 (SEQ ID NO:2) in a window between about 2 and about 6 hours after wounding. In another method of use, a patient with a chemical or thermal burn is treated intravenously with between 0.03 and 0.1 mg/kg of cP12 (SEQ ID NO:2) in a window between about 2 and about 6 hours after the burn. In another method of use, a patient with a chemical or thermal burn is treated intravenously with between 0.03 and 0.1 mg/kg of cP12 (SEQ ID NO:2) in a window between 2 and 6 hours after the burn. In another method of use, a patient with a chemical or thermal burn is treated intravenously with between 0.003 and 0.1 mg/kg of cP12 (SEQ ID NO:2) in a window of about 3 hours to about 5 hours after the burn. In another method of use, a patient with a chemical or thermal burn is treated intravenously with between 0.03 and 0.1 mg/kg of cP12 (SEQ ID NO:2) in a window about 4 hours after the burn. The phrase "about X hours", in the context of treatment with cP12 (SEQ ID NO:2) or another fibronectin fragment or peptide derivative of fibronectin, is defined as being within a half hour of X hours. For example, "about 4 hours" is defined as a value between 3.5 hours and 4.5 hours, inclusive.

The present compositions can be used either instead of or to supplement existing wound-care procedures such as skin grafting and tissue flaps, debridement, and the administration of anti-inflammatory, antibacterial and/or anti-pain medications.

Examples

The following examples further describe and demonstrate embodiments within the scope of the present invention. The examples are given solely for the purpose of illustration and are not to be construed as limitations of the present invention, as many variations thereof are possible without departing from the spirit and scope of the invention.

Studies of Timing of I.V. Treatment of Porcine Burns cP12 (SEQ ID NO:2):

For a pathobiology proof-of-principle study we used a validated porcine vertical injury progression burn model (Singer A J, Hirth D, McClain S A, Crawford L, Lin F, and Clark R A. Validation of a vertical progression porcine burn model. J Burn Care Res. 2011; 32(6):638-46). In short, while under general anaesthesia, twenty burns were created on the dorsal skin of four outbred female Yorkshire pigs (~25 kg) using a 2.5×2.5×7.5 cm, 150 gram aluminum bar equilibrated in an 80° C. water bath and applied for 20 s. The application of the 80° C. aluminum bar caused burn injury a little beyond mid-dermis but often progressed to full-thickness within 3-7 days. All burns were treated with petrolatum, and protected with Tegaderm. In some pigs, a fibronectin (FN)-derived peptide (P12) (SEQ ID NO:1) was infused over 30 min at 1, 2, and 4 h post-burn using doses of 0.003, 0.01 or 0.03 mg/kg. The infused P12 peptide (SEQ ID NO:1) was cyclized (cP12) (SEQ ID NO:2) to prevent exopeptidase digestion from amino- and carboxy-peptidases, which are common in the blood and skin.

Tissue specimens taken at 14 days after a 30 min infusion of cP12 (SEQ ID NO:2) doses at 0.003, 0.01, 0.03 or 0.1 mg/kg, where infusions began at 1, 4, 8, 12 and 24 h post-burn, have been fixed, stained with hematoxylin and eosin (H&E), and determined whether the surface of the wound was 100% re-epithelialized, i.e. wound closure obtained. The percent wounds totally re-epithelialized at each cP12 (SEQ ID NO:2) dose and each post-burn time of onset of a 30 min infusion are recorded in Table 1. The number of pigs used for each dose and time is denoted in Table 1 by parentheses. Each pig while under general anesthesia had 20 burn wounds administered on the back by a 2.5×2.5 aluminum bar heated to 80° C. and applied to the skin for 20 sec.

The effect of cP12 (SEQ ID NO:2) doses at 0.003, 0.01, 0.03 or 0.1 mg/kg at 4 h post-burn 30 min-infusion on percent wounds closed at 14d post-burn the 5 experiments performed under these conditions are shown in Table 2. The dates indicate the onset on each experiment, i.e. the date the pigs receive burns.

TABLE 1

Effect of cP12 dose and onset of post-burn 30 min-infusion*
on percent wounds closed at 14 d post-burn**

| Dose | Time | | | | |
| --- | --- | --- | --- | --- | --- |
|  | 1 h | 4 h | 8 h | 12 h | 24 h |
| 0.003 mg/kg | 17 (5) | 37 (3) | — | — | — |
| 0.01 mg/kg | 28 (8) | 65 (5) | 34 (5) | 40 (3) | 40 (3) |
| 0.03 mg/kg | 8 (8) | 25 (3) | — | — | — |
| 0.1 mg/kg | 25 (5) | 50 (2) | 28 (5) | 25 (3) | 17 (3) |
| 0 mg/kg (Compiled Controls) |  |  | 30 (20) |  |  |

*compiled data
**percent of wounds that were 100% re-epithelialization at 14 d post-burn
(n) indicates #animals

TABLE 2

Effect of cP12 dose at 4 h post-burn 30 min-infusion*
on percent wounds closed at 14 d post-burn

| Date of Experiment | 0 (Concurrent) | 0 (Compiled) | 0.003 mg/kg | 0.01 mg/kg | 0.03 mg/kg | 0.1 mg/kg |
| --- | --- | --- | --- | --- | --- | --- |
| 2013 Dec. 2 | 45 | 30 | 100 | 100 | 14 | — |
| 2014 Jun. 3 | 12 | 30 | 11 | 70 | 50 | — |
| 2014 Jul. 7 | 25 | 30 | 0 | 55 | 11 | — |
| 2014 Dec. 1 | 55 | 30 | — | 100 | — | 90 |
| 2015 Apr. 27 | 8 | 30 | — | 0 | — | 10 |

A number of embodiments of the invention have been described. Nevertheless, it will be understood that various modifications may be made without departing from the spirit and scope of the invention. Accordingly, other embodiments are within the scope of the following claims.

We claim:

1. A method of treating a patient with a wound selected from the group consisting of a surgical incision or extirpation, a traumatic injury, a thermal burn, a chemical burn, a lesion or ulceration of the patient's skin, mucosa, connective tissue, fascia, ligament, tendon, cartilage, nerve, or muscle, and a wound to the patient's bone, the method comprising:
  intravenously administering to the patient a therapeutically effective amount of a cyclized form of a polypeptide consisting of amino acids PSHISKYILRWRPK (SEQ ID NO:2), wherein the dosage is from 0.003 to 0.1 mg/kg and wherein the intravenous administration occurs from about 2 hours to about 6 hours after formation of the wound.

2. The method of claim 1, wherein the wound is a thermal burn or a chemical burn.

3. The method of claim 2, wherein the wound is a thermal burn.

4. The method of claim 2, wherein the intravenous administration is initiated about 4 hours after formation of the wound and the intravenous administration is given over about a half-hour period.

5. The method of claim 4, wherein the dosage is from 0.03 to 0.1 mg/kg.

6. The method of claim 3, wherein the intravenous administration is initiated about 4 hours after formation of the wound and the intravenous administration is given over about a half-hour period.

7. The method of claim 6, wherein the dosage is from 0.03 to 0.1 mg/kg.

8. The method of claim 1, wherein the polypeptide is cyclized by chemical crosslinking, chemical intramolecular ligation or enzymatic intramolecular ligation.

* * * * *